United States Patent

McLaughlin et al.

Patent Number: 5,125,903
Date of Patent: Jun. 30, 1992

[54] HEMOSTASIS VALVE

[75] Inventors: Brian E. McLaughlin, Salem, Mass.; Thomas R. Johnson, Milford, N.H.

[73] Assignee: Medtronic, Inc., Minneapolis, Minn.

[21] Appl. No.: 739,072

[22] Filed: Aug. 1, 1991

[51] Int. Cl.$^5$ ............................................. A61M 5/178
[52] U.S. Cl. .................................... 604/167; 604/256; 137/849; 251/149.1
[58] Field of Search ............... 604/167, 169, 237, 244, 604/256, 278; 137/843, 845, 849; 251/149.1

[56] References Cited

U.S. PATENT DOCUMENTS

| | | | |
|---|---|---|---|
| 3,848,579 | 11/1974 | Villa-Real | 604/237 |
| 4,000,739 | 1/1977 | Stevens | 128/214.4 |
| 4,424,833 | 1/1974 | Spector et al. | 137/849 |
| 4,430,081 | 2/1984 | Timmermann | 604/256 |
| 4,610,665 | 9/1986 | Matsumoto et al. | 604/167 |
| 4,610,674 | 9/1986 | Suzuki et al. | 604/282 |
| 4,626,245 | 12/1986 | Weinstein | 604/167 |
| 4,649,904 | 3/1987 | Krauter et al. | 128/6 |
| 4,673,393 | 6/1987 | Suzuki et al. | 604/167 |
| 4,682,981 | 7/1987 | Suzuki et al. | 604/158 |
| 4,723,550 | 2/1988 | Bales et al. | 128/344 |
| 4,726,374 | 2/1988 | Bales et al. | 128/344 |
| 4,798,594 | 1/1989 | Hillstead | 604/167 |
| 4,842,591 | 6/1978 | Luther | 604/283 |
| 4,842,592 | 6/1989 | Caggiani | 604/283 |
| 4,895,565 | 1/1990 | Hillstead | 604/167 |
| 4,909,798 | 3/1990 | Fleischhacker | 604/256 |
| 4,917,668 | 4/1990 | Haindl | 604/167 |

Primary Examiner—Cary E. O'Connor
Attorney, Agent, or Firm—Sandra S. Schultz; Joseph F. Breimayer

[57] ABSTRACT

A self-sealing, penetrable, hemostasis valve for a catheter introducer or the like which comprises an elastomeric gasket member having first and second opposed faces adapted to be secured in a valve housing, wherein faces define generally concave surfaces to reduce the central thickness of the gasket member, and a pin hole or slits extending through the first and second opposed faces generally at or through the central region of the gasket member. The generally concave opposed face surfaces are molded to possess a pair of convex cusp-shaped surfaces, each lying in about one-half of the generally concave surfaces, each convex cusp having an edge thereof passing generally through the central region of reduced thickness. The pair of generally convex, cusp-shaped surfaces on the first face is disposed at a 90 degree angle to the pair of generally convex, cusp-shaped surfaces on the second face. Preferably short intersecting slits extend through the reduced thickness central region oriented at a 45 degree angle to the 90 degree lines of intersection of the mating edges of the first and second cusp-shaped surfaces on each face of the elastomeric gasket member. The hemostasis valve of the present invention is preferably implemented in a percutaneous introducer comprising a longitudinally extended housing having a proximal open end for providing an entrance point for the introduction of elongated interventional devices and a second distal open end. An elongated tubular sheath is coupled to and extends distally from distal open end of housing. The hemostasis valve is located within the central passageway of the longitudinally extended housing, and proximal to a side port into the housing.

2 Claims, 2 Drawing Sheets

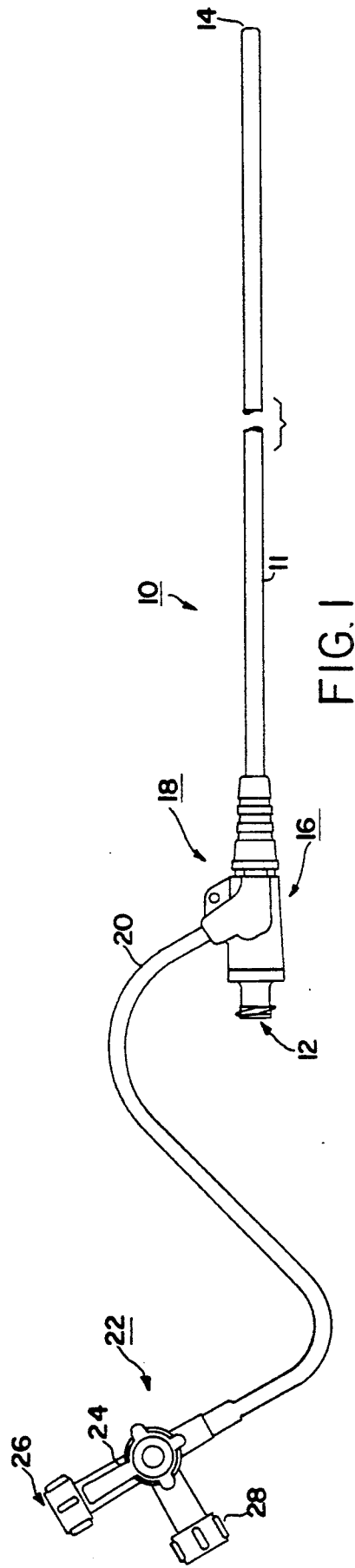
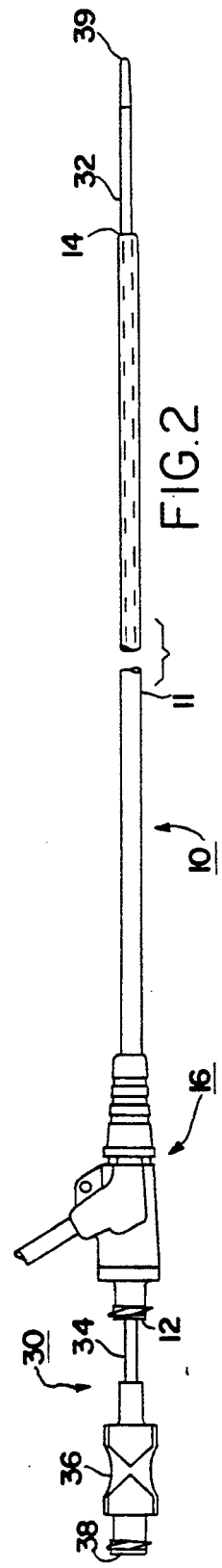
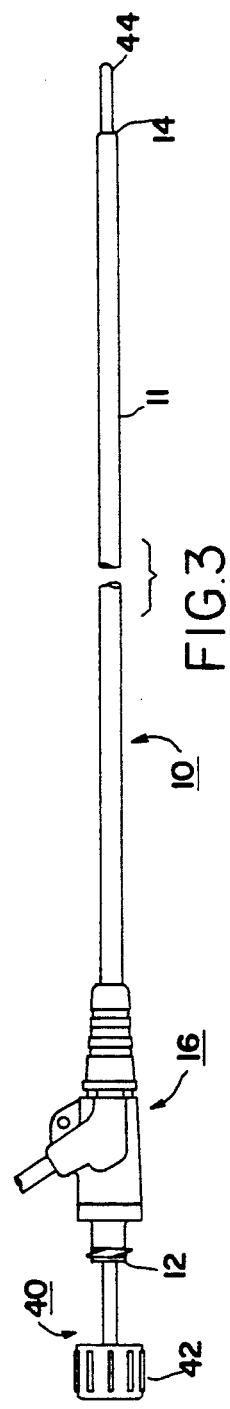
FIG.1
FIG.2
FIG.3

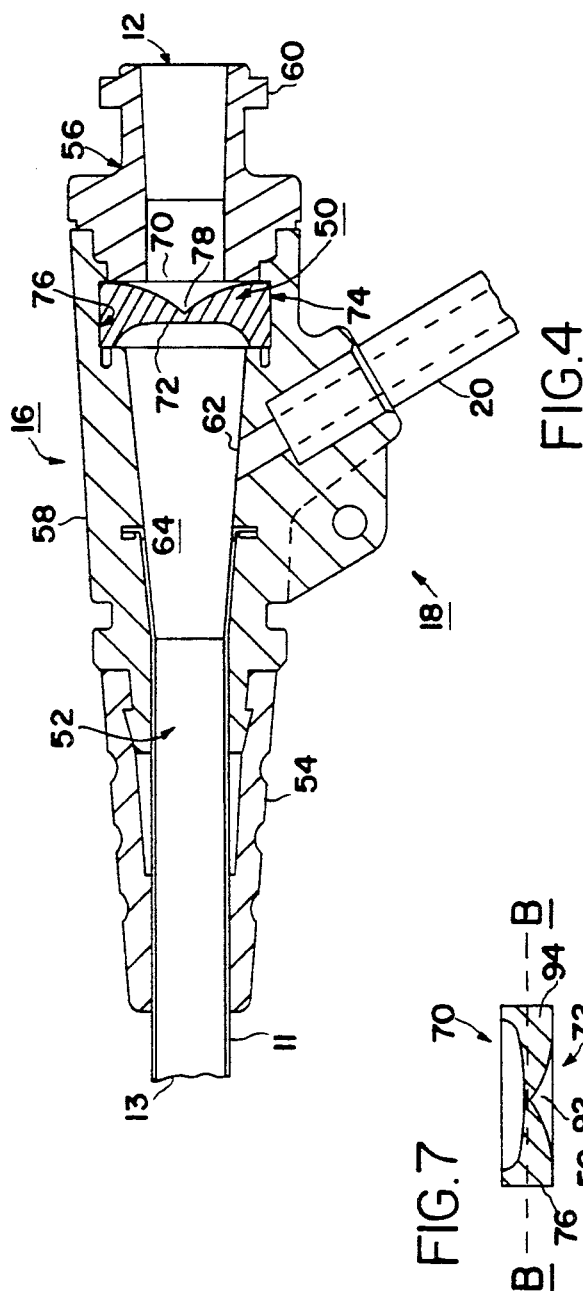
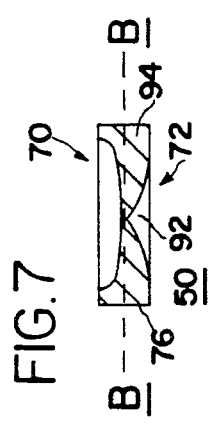
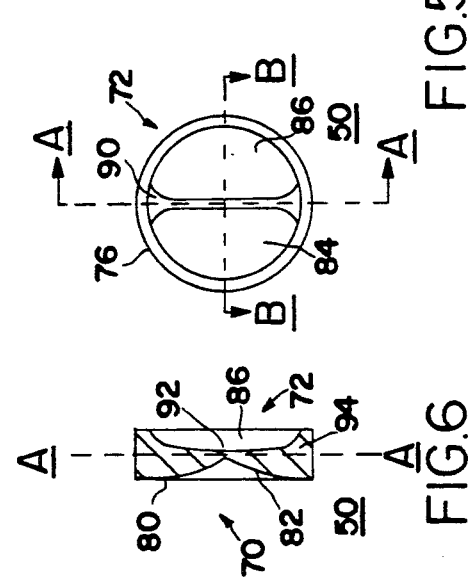
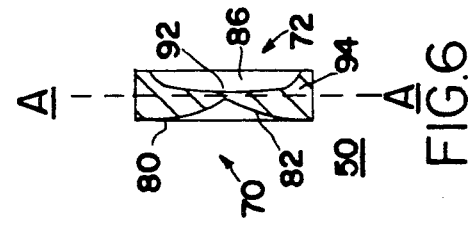
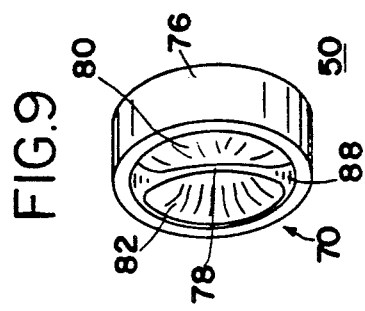
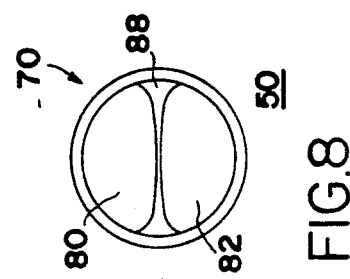

HEMOSTASIS VALVE

BACKGROUND OF THE INVENTION

1. Field of the Invention

The present invention relates to a hemostasis valve, and more particularly, to a hemostasis valve incorporated within an introducer assembly for enlarging and maintaining a percutaneous opening in a given arterial or venous vessel for the purpose of providing a pathway for the introduction of interventional devices.

2. Description of the Prior Art

The introduction of interventional devices into a given arterial or venous vessel for a variety of purposes, such as coronary angiography or for performing percutaneous transluminal coronary angioplasty (PTCA), as well as angiographic procedures, for example, where X-ray contrast fluid is inserted into the coronary artery, has been known for many years. Several techniques for introducing such catheters are available, including the cut-down method and the Seldinger technique. The Seldinger technique involves surgically opening a vein or artery with a needle, inserting a guide wire into the vein or artery through the lumen of the needle, withdrawing the needle, inserting over the guide wire a dilator located inside an associated hemostasis valve and sheath removing the dilator and inserting a catheter through the hemostasis valve and sheath into the blood vessel. In this process, care must be exercised to prevent introduction of air into the vessel and it is desirable to avoid leakage of blood out of the proximal end of the sheath. To avoid the risk of both "air embolism" and "blood contamination of the physician" modern introducers for the placement of such interventional devices as open and closed-end catheters, temporary pacing electrode catheters, guiding catheters, and angioplasty catheters, employ various types of hemostasis valves. Such hemostasis valves must be designed for use with more than one diameter catheter and guide wire that can be introduced within and through the hemostasis valve and outer sheath for the purposes listed above. Guide wires are of extremely small diameters—often less than 0.050 inch. However, many catheters are relatively larger in diameter. Therefore, the prior art has addressed many configurations of hemostasis valves attempting to provide an adequate seal at low and relatively higher blood pressure conditions for both air and blood while accommodating the wide range of diameters of devices inserted through the outer sheath.

Prior art hemostasis valves have, in many instances, been of the gasket sealing type, such as those shown in U.S. Pat. Nos. 4,000,739, 4,424,833, and 4,909,798, which comprise a pin hole and a Y-shaped slit, back-to-back gasket assembly in either one or two-piece parts. The first, doughnut-shaped, gasket is provided with a hole slightly smaller than the diameter of the catheter to be inserted, while the second gasket is provided with a Y-shaped slit. When guide wires or catheters which are too small in diameter are inserted into this hemostasis valve, the sealing advantages of the first doughnut-shaped gasket are no longer available because the larger diameter doughnut holes will not seal around the smaller diameter guide wire or catheter. The two gaskets may be provided as separate back-to-back piece parts or as a single piece part, but in either case, are intended to reduce the possibility that blood would escape the hemostasis valve as the tip of the introduced instrument is withdrawn. Thus, the redundancy of the two seals is expected to reduce such leakage.

In attempts to improve on the back-to-back hole and Y-shaped slit seals, it has been proposed in U.S. Pat. Nos. 4,610,665, 4,610,674, 4,626,245, and 4,673,393 to provide hemostasis valves in either single or multiple combinations where the disk-like valve is provided with a first slit open only to one of the end faces thereof and the second slit open only to the other of the end faces thereof, intersecting at roughly the center of the disk so that a pin hole is effected through the end faces at the intersecting point of the two slits. The end faces of the disk-shaped valve are flat and parallel to one another.

In a further variation on the Y-shaped slit of the '739 patent, for example, and the criss-crossing partial slits of the '665 patent, for example, it has also been proposed in U.S. Pat. Nos. 4,798,594 and 4,895,565 to provide a Y-shaped slit through the disk-shaped hemostasis valve body by pressing a die through the body while simultaneously rotating the die or the body so as to provide a continuous Y-shaped slit from one surface to the other surface of the body but wherein the entrance and exit points are transposed rotationally from one another. In the '569 patent, the opposing faces of the disk-shaped body are concave, resembling a dual concave lens having the rotationally translated Y-shaped slit extending therethrough.

In still further attempts to accommodate various diameter therapeutic instruments and varying blood pressure between venous and arterial applications, introducers have employed hemostasis valves of the Tuohy-Borst type. For example, U.S. Pat. Nos. 4,726,374 and 4,723,550 provide at least one hemostasis valve assembled within a housing proximal to the side port, where the housing may be tightened down on the resilient gasket material of the valve to compress it to provide variable pressure seal to the interventional device passing therethrough.

In yet still another approach to providing a suitable seal under the varying conditions of usage encountered in practice, it has also been proposed in U.S. Pat. No. 4,917,668 to spring-load the resilient gasket valve member with one or more spring elements to augment the natural resilience of the gasket material.

The hemostasis valves described above all represent departures from and attempts to overcome deficiencies in flat-sided disk-shaped gaskets involving reduced diameter holes, slits and crossed slits therethrough to accommodate instruments passed through the valve housing and sheath, constituting an introducer sheath. It remains desirable to provide a simple, easy to manufacture hemostasis valve that is reliable in preventing leakage of blood or air and which possesses a feel of smoothness during insertion and withdrawal of all of the aforementioned varying diameter and material instruments therethrough.

The physician is interested in the ability of the valve to seal while not impeding advancement or rotation of the interventional device. The physician desires to be able to feel the movement of the distal end of the interventional device through manipulation of the proximal end or portion thereof. Frictional drag or compression of the interventional device impedes the ability to feel the distal movement thereof.

SUMMARY OF THE INVENTION

It is therefore an object of the present invention to provide a hemostasis valve, particularly in a device for enlarging and maintaining a percutaneous opening to a given arterial or venous vessel for the purpose of providing a pathway for the introduction of interventional devices.

It is a further object of the present invention to provide a simple, inexpensive, single piece molded hemostasis valve in a percutaneous catheter introducer.

It is a further object of the present invention to provide a hemostasis valve which is universally applicable for use in a given percutaneous catheter introducer to accommodate a variety of interventional devices having a variety of diameters, without leakage of blood or air therethrough.

It is still another object of the present invention to construct a hemostasis valve and percutaneous catheter introducer which will permit the introduction and passage of interventional devices therethrough, having a wide variety of diameters while allowing the insertion and withdrawal of such devices without undue friction or pressure and providing the physician with the ability to feel the advancement of the device distally, through the chosen venous or arterial system.

These and other objects of the invention are obtained by constructing a hemostasis valve which comprises an elastomeric gasket member having a first and second opposed faces and adapted for securement in a valve housing, wherein at least one of said faces defines a generally concave surface to reduce the central thickness of the gasket member, and a pin hole or slits extending through said first and second opposed faces generally at or through the central region of the gasket member, wherein the generally concave surface of the face of the elastomeric gasket member is molded to possess a pair of convex cusp-shaped surfaces, each lying in about one-half of the generally concave surface, each convex cusp having an edge thereof meeting generally in the central region of reduced thickness. More particularly, the present invention contemplates the provision of a similar generally concave surface with a pair of symmetrical, opposed, generally convex cusp-shaped surfaces composing the second face of the elastomeric gasket member, wherein the orientation of the first pair of generally convex cusp-shaped surfaces on the second face are disposed at a 90° angle to the generally convex, cusp-shaped surfaces of the first face. Preferably short intersecting slits extend through the reduced thickness central region oriented at a 45° angle to the 90° lines of intersection of the mating edges of the first and second cusp-shaped surfaces on each face of the elastomeric gasket member.

The hemostasis valve of the present invention is preferably implemented in a percutaneous introducer comprising a longitudinally extended housing having a proximal open end for providing an entrance point for the introduction of elongated interventional devices and a second opposing open end. An elongated tubular sheath is coupled to and extends distally from said distal open end of said housing. The hemostasis valve is located within the central passageway of the longitudinally extended housing, and proximal to a side port into the housing.

By employing this hemostasis valve, it is possible to use varying diameter interventional devices while maintaining adequate sealing and feel for a wide range of interventional devices introduced therethrough into a chosen venous or arterial system. The whole design of the hemostasis valve allows for it to be molded as a single piece gasket of tear-resistant elastomeric material which may be subsequently pin hole punched through the central portion of reduced thickness and/or slit for a predetermined distance from the central portion along the generally transversely oriented facing edges of the pair of convex cusps molded into the generally concave opposing faces of the gasket. In the embodiment involving slitting along the aforementioned lines or edges, the valve operates as a quad-cuspid leaflet valve wherein the cusps are thinnest at their point of common joinder in the central region of the gasket and become thicker in a direction extending radially from the central portion of the gasket.

BRIEF DESCRIPTION OF THE DRAWINGS

The above and still further objects, features, and advantages of the present invention will become apparent from the following detailed description of the preferred embodiments, taken in conjunction with the accompanying drawings in which like elements are referenced by like numbers, and in which:

FIG. 1 is a side plan view of an introducer assembly in which the hemostasis valves of the present invention may be employed;

FIG. 2 is a side plan view of a dilator advanced partially into the introducer of FIG. 1;

FIG. 3 is a side plan view of an obturator advanced partially into the introducer of FIG. 1;

FIG. 4 is a cross-sectional side view of the valve housing of the introducer depicted in FIG. 1 showing the components thereof, including the hemostasis valve;

FIG. 5 is a view of a first opposed surface of a first embodiment of the valve gasket of the present invention;

FIG. 6 is a side cross-sectional view of the valve gasket of FIG. 5 taken along section A—A;

FIG. 7 is a side cross-sectional view of the valve gasket of FIG. 5 taken along section B—B;

FIG. 8 is a view of the second opposed surface of the valve gasket of FIG. 5; and FIG. 9 is a perspective view of the valve gasket of FIGS. 5–8.

DETAILED DESCRIPTION OF THE PREFERRED EMBODIMENTS

The improved hemostasis valve of the present invention is preferably incorporated in a PTCA introducer system.

In PTCA, stenotic regions of coronary blood vessels are dilated by advancing a dilatation catheter through blood vessels into the stenotic region. The dilatation catheter advances over a guide wire, which itself is advanced in successive steps to the stenotic region. After placing the catheter in the desired position in the stenotic region, the guide wire may be removed. In fixed guide wire dilatation catheter PTCA devices, both the guide wire and the catheter are simultaneously advanced through a further guide catheter which in turn is advanced through the outer sheath of the introducer.

Conventional introducers include the outer sheath extending distally from a valve housing. A side port in the valve housing distal to the valve itself is provided for the perfusion and aspiration of fluids through the sheath. The introducer sheath maintains the percutaneous opening initially made with other devices, such as a hypodermic needle or scalpel, and provides an entrance point for a dilator and obturator, as well as the aforementioned listed catheters and guide wires. The entrance point is located in the valve housing proximal to the hemostatic valve so that when the dilator, obturator, catheter or guide wire is introduced, it extends through the length of the sheath and out its distal opening, which is positioned in use a distance within the vein or artery accessed previously.

The introduction of the introducer sheath is accomplished, as mentioned above, by the dilator advancing over the guide wire, both of which are advantageously passed through the introducer sheath and valve. Once the introducer sheath is advanced a sufficient distance within the chosen vessel, the guide wire and dilator are removed in favor of the insertion of the therapeutically applied catheter system.

An obturator is provided to prevent kinking of and to minimize blood stagnation within the sheath when the sheath is left indwelling in the patient between therapeutic procedures. The obturator is a solid flexible rod terminating in a blunt, rounded tip on its distal end and a male luer-lock cap on its proximal end for attachment to the female luer-lock at the proximal entrance point of the introducer sheath. Specific features of the introducer system in which the hemostasis valve of the present invention may be incorporated are described hereinafter in reference to the drawings of the preferred embodiments.

Turning now to the drawings, FIGS. 1 to 3 illustrate in side views the PTCA catheter introducer 10 which has a proximal input port 12 for the introduction of the interventional devices described above and a distal opening 14 through which the interventional devices are advanced into the accessed vein or artery. The introducer includes a valve housing 16 having a side port 18 coupled by hose 20 to a stop cock assembly 22. The three-way stop cock assembly 22 permits continuous flushing or periodic aspiration and allows changes to be made from IV drip to emergency medications or pressure monitoring without disconnecting or reconnecting IV tubes in a well known fashion. Generally, the side port 22 is employed to facilitate perfusion and aspiration of fluids through the sheath 11.

The side port 18 is open within the valve body 16 to the distal opening 14 and is closed off by operation of a stop cock valve 24 that may be manually actuated to three positions. In first and second positions, the ports 26 or 28 may be opened through the lumen of the flexible tube 20 to the side port 18. In a third position, both ports 26 and 28 may be closed, all in a fashion well known in the prior art.

The proximal opening 12 of the valve housing 16 is preferably fabricated having a male luer-lock connector or fitting that mates with the knobs of the dilator and obturator depicted in relation to the introducer 10 in FIGS. 2 and 3, respectively.

Turning to FIG. 2, the dilator 30 is depicted almost entirely advanced through the lumen of the sheath 11 so that its distal end portion 32 extends out the distal opening 14 and its proximal portion 34, the luer-lock female connector 36, and proximal port 38 are positioned to be advanced distally to be compression fit into the proximal opening 12 of valve body 16.

As explained above, dilator 30 is a hollow tubular device which enlarges the percutaneous opening initially made by other devices, such as hypodermic needles or scalpels, and it contains a single concentric lumen of sufficient diameter to allow for free movement of an appropriate sized guide wire within. Thus, the proximal opening 38 of the dilator 30 provides access to interventional devices which are passed through the lumen of the dilator 30 and out its distal portion 32 and distal opening 39 and thereafter into the accessed blood vessel. The distal portion 32 of the dilator is tapered to provide a smooth transition over the guide wire advanced therethrough. The proximal opening 38 is created by a further male luer-lock extending proximally from the connector 36.

Turning now to FIG. 3, an obturator 40 is depicted extending into the opening 12 of the valve housing 16 and extending through the lumen of the elongated sheath 11 and out its distal opening 14. As described above, obturator 40 is a solid, blunt-tipped rod 44 which may be inserted into the lumen of the sheath 11 to occupy it during periods of time that the introducer 10 is not being used for medical procedures. The obturator 40 includes a knob 42 which possesses a female luer-lock receptacle adapted to be screwed onto the male luer-lock threads surrounding the opening 12 of the valve body 16 of the PTCA introducer 10.

The above-described introducer 10 and its associated dilator 30 and obturator 40 is conventional in the prior art in which the hemostasis valve of the present invention may be implemented. Turning now to FIG. 4, the valve housing 16 is depicted in cross-section in order to illustrate the location of the hemostasis valve gasket member 50 of the present invention. The valve housing 16 is coupled to the flexible, transparent tubing 20 at the side port 18 and to the thin walled, elongated sheath 11 which extends distally from a distal opening 52 of the housing body 58 as shown in FIGS. 1 to 3. A relatively soft elastomeric strain relief 54 surrounds the inner section of the sheath 11 and the distal portion of the valve housing 16 defining the distal opening 52.

The proximal connector fitting 56 is coupled to the housing body 58 and provides the opening 12 defined by the male luer-lock connector 60 described hereinbefore. The side port 18 includes a bore 62 intersecting the inner chamber 64 of the elongated housing body 58 distal to the location of the hemostasis valve gasket member 50. Thus, the hemostasis valve housing 16, comprising the proximal fitting 56, the elongated chamber 64 surrounded by the body 58 and the distal opening 52 and strain relief 54, defines an elongated chamber having proximal and distal ends and supports the hemostasis valve gasket member 50 therebetween. The gasket member 50 therefore normally seals chamber 64 from opening 12.

The hemostasis valve gasket member 50 is generally disk-shaped having first and second opposite surfaces 70 and 72 and an annular outer periphery 76 which is fitted into a circular seat 74 of body 58 and retained there by pressure exerted against the peripheral portions of surfaces 70, 72 and by the proximal male luer-lock fitting 56. Ultrasonic welding is employed during assembly to attach the fitting 56 to the distal portion of the body 58 and compress the peripheral portions of the surfaces 70, 72 and compress the outer periphery 76 against the seat 74.

The hemostasis valve gasket 50 also is provided with a pin hole or a pair of slits described hereinafter in reference to FIGS. 5 to 9 through which the distal ends of the dilator 30, obturator 40 or other interventional device may be advanced by compression of the elastomeric material of the gasket 50 around the periphery of the body of the interventional device passing therethrough. Thus, as the interventional devices are introduced into the opening 12, they pass through the centrally disposed pin hole or slit opening 78, through the chamber 64, the opening 52 and down through the lumen 13 of the tube 11 which constitutes the portion of the introducer sheath advanced into the blood vessel of interest.

Turning now to FIGS. 5 to 8, they depict plan and cross-sectional views of the hemostasis valve gasket member 50 showing how the opposing faces 70 and 72 are configured in accordance with the preferred embodiment of the present invention. In a preferred embodiment of the present invention, the over-all diameter of the disk-shaped valve gasket member 50 is in the range of 0.312 inches and its maximal thickness is in the range of 0.090 inches. The opposing surfaces 70 and 72 are generally concave although each surface possesses a pair of relatively convex cusps which are denoted as 80, 82 on surface 70 and 84, 86 on surface 72. The relatively convex cusps are separated by a linear edge region denoted as 88 on face 70 and 90 on face 72. As shown in cross-section FIGS. 6 and 8, the relatively convex cusps increase in thickness from the central region to the peripheral region of the disk-shaped valve gasket 50.

This relationship of the relatively convex cusps in the concave opposing surfaces 70 and 72 are oriented in the preferred embodiment at 90 degrees to one another so that the intersecting central region 92 is relatively thinner than the peripheral region 94 of the opposite surfaces 70, 72, having a thickness of about 0.008 inches.

Preferably, a pair of criss-cross slits 78 are formed by a punch press operation after the gasket 50 is molded. The slits 78 are oriented at 90 degrees to one another, but at 45 degrees relatively speaking, to the linear portions 88 and 90 of each face 70 and 72. Each slit is preferably about 0.030 inches long.

Alternatively, a pin hole may be made at the center 92 of the disk-shaped gasket to facilitate the passage of the interventional devices through the hemostasis valve as described above. The choice of employing slits or pin holes largely depends on the feel that is desired in the passage of the interventional devices through the valve gasket 50.

FIG. 9 is a perspective view of face 70 of valve gasket 50 showing the generally concave centrally disposed region of face 70, the opposed generally convex cusps 80 and 82 and the intersecting edge 88 between the cusps. The criss-cross intersecting slits 78 are shown passing through the central region 92 and intersecting edge 88.

The valve gasket member 50 is preferably fabricated by transfer molded of polyisoprene from polyisoprene gum stock, although it could be fabricated from silicone rubber, natural rubber or thermoplastic elastomers, e.g., injection moldable synthetic rubber compounds. The valve gasket 50 preferably has a Shore hardness of 40A±5A, although a wider range of approximately 30A to 50A may be usable in practice.

The assembled valves are tested under pressure to detect any leakage through the centrally disposed slits with and without interventional devices of varying diameters extending therethrough. In its intended use environment, the valve may be subjected to blood pressures of up to 300 mm Hg, but testing is conducted at 600 mm Hg. The valve 50 does not leak at 600 mm Hg pressure, with or without the interventional devices in place.

As many apparently widely different embodiments of the present invention can be made without departing from the spirit and scope thereof, it is to be understood that the invention is not limited to the specific embodiments thereof except as defined in the appended claims.

What is claimed is:

1. A medical instrument for the percutaneous introduction of an interventional device comprising:

a valve housing having a proximal opening for providing an entrance point for the introduction of an interventional device, and a central chamber communicating with an opposite distal opening; and a valve comprising a one-piece seal means located within said central chamber and having a general disk-shape with opposed first and second surfaces, a central region having a pin hole or slit extending between said surfaces and a peripheral region adapted to be coupled in a sealing relation with said central chamber for normally sealing the flow of blood or air at ambient air and blood pressures encountered in actual use, wherein said first and second surfaces are generally concave and provide a central area with a thickness reduced from the periphery thereof, each of said concave surfaces further comprising a pair of convex cusp surfaces, each having intersecting edges extending from the periphery to the central region of each face of said seal means, whereby said seal means receives and seals around the periphery of an interventional device introduced into said entrance point through said pin hole or slit and out said opposite distal opening.

2. A percutaneous catheter introducer with hemostasis valve comprising:

a longitudinally extending valve housing having a proximal opening for providing an entrance point for the introduction of an interventional device, and a central longitudinal chamber communicating with an opposite distal opening;

an elongated sheath member having proximal and distal ends and a lumen extending therebetween, said proximal end coupled with said distal opening of said valve housing; and a one-piece seal means stationarily located within said central longitudinal chamber and having a general disk-shape with opposed first and second surfaces, a central region and a peripheral region adapted to be coupled in a sealing relation with said central longitudinal chamber for normally sealing the flow of blood or air at ambient air and blood pressures encountered in actual use, wherein said first and second surfaces are generally concave and provide a central area with a thickness reduced from the periphery thereof, each of said concave surfaces further comprising a pair of convex cusp surfaces, each having intersecting edges extending from the periphery to the central region of each face of said seal means.

* * * * *